United States Patent [19]

Audousset et al.

[11] Patent Number: 5,538,516
[45] Date of Patent: Jul. 23, 1996

[54] COMPOSITION FOR THE OXIDATION DYEING OF KERATINOUS FIBRES, COMPRISING A PARA-PHENYLENEDIAMINE DERIVATIVE AND A META-AMINOPHENOL DERIVATIVE, AND DYEING PROCESS USING SUCH A COMPOSITION

[75] Inventors: Marie-Pascale Audousset, Asnieres; Jean Cotteret, Verneuil s/Seine, both of France

[73] Assignee: L'Oreal, Paris, France

[21] Appl. No.: 361,679

[22] Filed: Dec. 22, 1994

[30] Foreign Application Priority Data

Jan. 24, 1994 [FR] France .................................. 94 00702

[51] Int. Cl.⁶ ........................................................ A61K 7/13
[52] U.S. Cl. ...................... 8/412; 8/406; 8/408; 8/410; 8/416; 8/421
[58] Field of Search .............................. 8/405, 406, 408, 8/410, 412, 416, 421

[56] References Cited

U.S. PATENT DOCUMENTS

| | | | |
|---|---|---|---|
| 4,065,255 | 12/1977 | Andrillon et al. | 8/10.2 |
| 4,289,495 | 9/1981 | Bugaut et al. | 8/406 |
| 4,311,478 | 1/1982 | Bugaut et al. | 8/411 |
| 4,324,553 | 4/1982 | Bugaut et al. | 8/412 |
| 4,566,875 | 1/1986 | Grollier et al. | 8/412 |
| 4,840,639 | 6/1989 | Husemeyer et al. | 8/410 |
| 4,904,275 | 2/1990 | Grollier | 8/412 |

FOREIGN PATENT DOCUMENTS

| | | |
|---|---|---|
| 0007537 | 2/1980 | European Pat. Off. . |
| 0400330 | 12/1990 | European Pat. Off. . |
| 2315255 | 1/1977 | France . |
| 2018808 | 10/1979 | United Kingdom . |
| 2085483 | 4/1982 | United Kingdom . |
| 2239265 | 6/1991 | United Kingdom . |

*Primary Examiner*—Paul Lieberman
*Assistant Examiner*—Caroline L. Dushek
*Attorney, Agent, or Firm*—Finnegan, Henderson, Farabow, Garrett & Dunner

[57] ABSTRACT

A composition for the oxidation dyeing of keratinous fibres, in particular human keratinous fibres such as hair, of the type comprising, in a medium which is suitable for dyeing, at least one para-phenylenediamine oxidation dye precursor which is substituted in the 2 position on the benzene ring or an acid addition salt thereof, and, at least one specific meta-aminophenol coupling agent or an acid addition salt thereof. The use of this composition for dyeing keratinous fibres, in particular human keratinous fibres such as hair.

21 Claims, No Drawings

COMPOSITION FOR THE OXIDATION DYEING OF KERATINOUS FIBRES, COMPRISING A PARA-PHENYLENEDIAMINE DERIVATIVE AND A META-AMINOPHENOL DERIVATIVE, AND DYEING PROCESS USING SUCH A COMPOSITION

The present invention is directed to a composition for the oxidation dyeing of keratinous fibres, in particular human keratinous fibres such as hair, which composition comprises, in combination, at least one para-phenylenediamine which is substituted in 2 position on the benzene ring, and one meta-aminophenol, which are of the structures provided below in the description. The present invention is also directed to the use of such a composition.

It is known to dye keratinous fibres, and in particular human keratinous fibres such as hair, with dye compositions containing oxidation dye precursors, in particular ortho- or para-phenylenediamines, ortho- or para-aminophenols, generally referred to as "oxidation bases," and coupling agents, also referred to as coloration modifiers, more particularly meta-phenylenediamines, meta-aminophenols and meta-diphenols. These compositions enable the "background" colorations obtained with the product of condensation of the oxidation bases to be modified and to be enriched with glints.

In the field of oxidation dyeing of hair, oxidation dye precursors and coupling agents which are capable of generating, when they are combined, a red coloration which has satisfactory resistance to light, to washing, to inclement weather, to perspiration and to the various treatments to which hair may be subjected, are actively sought.

Hitherto, these colorations were obtained with dyes based on para-phenylenediamine. However, the use of para-phenylenediamine is currently being questioned for toxicological reasons.

After considerable research conducted in this area, it has been discovered that it is possible to obtain new non-toxic dyes which generate colorations ranging from red to purple, and which are both intense and resistant, by combining a para-phenylenediamine which is substituted in the 2 position on the benzene ring with a meta-aminophenol, which compounds have structures which are respectively defined below.

The present invention is thus directed to a composition for the oxidation dyeing of keratinous fibres, in particular human keratinous fibres such as hair, comprising a medium suitable for dyeing, the medium containing at least one para-phenylenediamine oxidation dye precursor of formula (I):

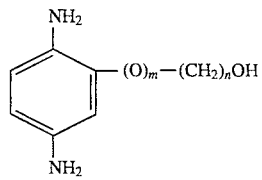

in which m is an integer equal to zero or 1; n is an integer ranging from 1 to 4 inclusively; and/or at least one acid addition salt thereof; and, at least one meta-aminophenol coupling agent of formula (II):

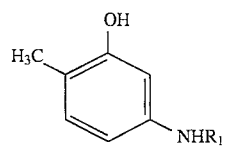

in which $R_1$ represents an alkyl radical containing from 1 to 2 carbon atoms or a β-hydroxyalkyl radical containing from 2 to 3 carbon atoms; and/or at least one acid addition salt thereof; with the proviso that when, in formula (I), m represents zero, and when, in formula (II), $R_1$ represents a β-hydroxyethyl radical, the dye composition is free of 3-methyl-para-aminophenol, 2-methyl-para-aminophenol and 2-hydroxymethyl-para-aminophenol.

The present invention is also directed to an oxidation dyeing composition for keratinous fibres, in particular human keratinous fibres, which is a ready-to-use composition, which further comprises an oxidizing agent and has a pH ranging from 3 to 11.

The present invention also contemplates a process for dyeing keratinous fibres, in particular human keratinous fibres, comprising the steps of: (i) applying to the fibres the dyeing composition as defined above; and (ii) using an oxidizing agent, the oxidizing agent being applied to the fibres simultaneously with or subsequent to the dyeing composition, to develop the colour of the dyeing composition in an acidic, neutral or alkaline medium. The oxidizing agent can be added to the dyeing composition only at the time of use or can be present in a composition (B) applied simultaneously or sequentially in a separate manner.

The present invention further contemplates a kit for dyeing keratinous fibres, in particular human keratinous fibres, comprising at least two compartments, one of the compartments containing a dyeing composition as defined above, and another of the compartments containing a composition (B) containing an oxidizing agent in a medium suitable for dyeing.

A further embodiment of the present invention includes a process for dyeing keratinous fibres, in particular human keratinous fibres, comprising the steps of: (i) applying to the fibres a dyeing composition as defined above, the dyeing composition being obtained from a kit for dyeing keratinous fibres comprising at least two compartments, one of the compartments containing the dyeing composition as defined above and another of the compartments containing a composition (B) containing an oxidizing agent in a medium suitable for dyeing; and (ii) using the oxidizing agent and the suitable dyeing medium, the agent and the medium being applied to the fibres simultaneously with or subsequent to the dyeing composition, to develop the colour of the dyeing composition in the medium.

The composition and process of the present invention are used for the oxidation dyeing of keratinous fibres in general. The preferred form of keratinous fibres taught by this invention is human keratinous fibres, such as hair.

The new dyes thus obtained make it possible to achieve colorations ranging from red to purple, which colorations are sustained, non-toxic and resistant at the same time to light, to washing, to inclement weather, to perspiration and to the various treatments to which hair may be subjected. Most particularly, they are very resistant to shampoos. Other characteristics, aspects, aims and advantages of the present invention will emerge more clearly upon reading the description and the examples which follow.

The acid salts which may be used according to the present invention are preferably independently chosen from hydrochlorides, sulphates, hydrobromides and tartrates.

Among the oxidation dye precursors which may be used within the context of the present invention, the following compounds are preferably used:
2-(hydroxymethyl)-para-phenylenediamine;
2-(β-hydroxyethyl)-para-phenylenediamine;
2-(β-hydroxyethoxy)-para-phenylenediamine; and the acid addition salts thereof. The concentration of this (these) precursor(s) or of the acid addition salts thereof may preferably range from 0.01% to 10% by weight approximately relative to the total weight of the dye composition, and more preferably range from 0.05% to 5% by weight approximately.

Among the coupling agents of formula (II), it is preferable to use 2-methyl-5-N-(β-hydroxyethylamino)phenol or one of the acid addition salts thereof. The concentration of coupling agent(s) of formula (II) or of acid addition salts thereof may preferably range from 0.005% to 3% by weight approximately relative to the total weight of the dye composition, and more preferably range from 0.05% to 2% by weight approximately.

A particularly preferred oxidation dye composition according to the invention comprises, as an oxidation dye precursor, 2-(β-hydroxyethyl)-para-phenylenediamine or an acid addition salt thereof; and, as a coupling agent, 2-methyl-5-N-(β-hydroxyethylamino)-phenol or an acid addition salt thereof; with the proviso that this dye composition is free of an additional oxidation dye precursor selected from 3-methyl-para-aminophenol, 2-methyl-para-aminophenol and 2-hydroxymethyl-para-aminophenol. Another dye composition which is also particularly preferred comprises, as an oxidation dye precursor, 2-(β-hydroxyethoxy)-para-phenylenediamine or an acid addition salt thereof; and, as a coupling agent, 2-methyl-5-N-(β-hydroxyethylamino)phenol or an acid addition salt thereof.

The oxidizing agent may preferably be chosen from hydrogen peroxide, urea peroxide, alkali metal bromates and persalts such as perborates and persulphates. More preferably, the oxidizing agent is hydrogen peroxide.

Composition (A), which contains the combination of the dyes as described above, may have a pH which preferably ranges from 3 to 11. The pH may be adjusted to the desired value either by using basifying agents which are conventionally used for dyeing keratinous fibres, such as aqueous ammonia, alkali metal carbonates, alkanolamines such as, for example, mono-, di- and triethanolamines and the derivatives thereof, sodium hydroxide or potassium hydroxide, or the compounds of formula:

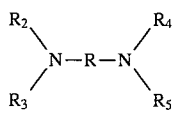

in which R is a propylene residue which is optionally substituted with a hydroxyl group or a $C_1$–$C_4$ alkyl radical; $R_2$, $R_3$, $R_4$ and $R_5$ represent, simultaneously or independently of each other, a hydrogen atom, a $C_1$–$C_4$ alkyl radical or a $C_1$–$C_4$ hydroxyalkyl radical; or using standard acidifying agents, such as inorganic or organic acids, such as for example, hydrochloric acid, tartaric acid, citric acid and phosphoric acid.

The pH of the composition (B) containing the oxidizing agent as defined above is such that, after mixing with the composition (A), the pH of the composition applied to the keratinous fibres, in particular human keratinous fibres, preferably ranges from 3 to 11. The pH can be adjusted to the desired value using acidifying agents, or possibly basifying agents, which are well-known in the state of the art, such as those described above. The oxidizing composition (B) preferably consists of a solution of hydrogen peroxide.

According to a preferred embodiment of the dyeing process of the present invention, the dye composition (A) described above is mixed, at the time of use, with an oxidizing solution in a sufficient amount to develop a coloration. The mixture obtained is then applied to the keratinous fibres, in particular human keratinous fibres, and is left to stand for preferably 5 to 40 minutes, and more preferably for 15 to 30 minutes, after which the fibres are rinsed, washed with shampoo, rinsed again and dried.

In addition to the dyes defined above, the dye compositions may also contain other direct dyes and/or coupling agents, especially in order to modify the shades or to enrich them with glints.

The dye compositions may also contain antioxidants. The antioxidants may preferably be chosen from sodium sulphite, thioglycolic acid, thiolactic acid, sodium bisulphite, dehydroascorbic acid, hydroquinone, 2-methylhydroquinone, tert-butylhydroquinone and homogentisic acid, and are generally present in proportions preferably ranging from approximately 0.05% to 1.5% by weight relative to the total weight of the composition.

In another preferred embodiment, the dye compositions may also contain surface-active agents which are well-known in the art, in proportions preferably ranging from approximately 0.5% to 55% by weight, and more preferably from 2% to 50% by weight, relative to the total weight of the composition; organic solvents in proportions preferably ranging from approximately 1% to 40% by weight, and more preferably from 5% to 30% by weight, relative to the total weight of the composition; or any other adjuvant which is cosmetically acceptable and is known in the prior art in the oxidation dyeing of hair.

The composition which is applied to the hair may preferably be provided in various forms, such as in the form of a liquid, a cream, a gel or any other form which is suitable for dyeing keratinous fibres and in particular human hair. The composition may preferably be packaged under pressure in an aerosol can in the presence of a propellant and be capable of forming a foam.

Concrete examples illustrating the invention will now be given. To begin with, a definition will be given of the tests used to evaluate the performance of the oxidation dyes according to the invention, regarding their resistance to perspiration, to light, to shampoos, to inclement weather or to permanent-waving.

Resistance to perspiration:

A synthetic sweat solution of the following composition was used: 10 g of NaCl, 1 g of potassium hydrogen phosphate, 0.25 g of histidine, lactic acid to give pH=3.2 and distilled water to make up to 100 g.

The locks of dyed hair were immersed in the sweat solution which was contained in a crystallizing dish covered with a watch glass, and were left for a period of 20 to 50 hours at 37° C. The locks were then rinsed and dried.

Resistance to light (Xenotest)

The dyed hair was attached to a support (cardboard or plastic). These supports were arranged on sample holders which rotated around a Xenon lamp for a duration ranging from 20 to 80 hours, at a moisture content ranging from 25 to 75% RH (Relative Humidity) and at a temperature of 25° C.

Resistance to shampoos (Ahiba-Texomat machine):

Locks of dyed hair were placed in a basket which was immersed in a solution of a standard shampoo. The basket was subjected to an up-and-down movement of variable frequency and to a rotational movement, which reproduced the action of manual rubbing, thereby causing the formation of foam.

After a treatment time of 3 minutes, the locks were removed and then rinsed and dried. The dyed locks may have been subjected to several consecutive shampoo tests.
Resistance to inclement weather (Combined test):

The dyed locks were exposed to strong light (Xenotest 40 h), at a relative humidity of 60%, and simultaneously, every 12 hours and for a duration of 20 minutes, they were sprayed with water.
Resistance to permanent-waving:

The dyed locks were immersed in Dulcia Vital permanent-wave reducing solution (L'Oréal), of strength ranging from 1 to 3, for a duration ranging from 10 to 20 minutes; the locks were rinsed and then soaked in a fixing (oxidizing) solution for 5 minutes. After rinsing with water, washing with standard shampoo and rinsing with water, they are dried.

EXAMPLE 1

The following dye composition, in accordance with the invention, was prepared:

| | |
|---|---|
| 2-(β-Hydroxyethyl)-para-phenylenediamine dihydrochloride | 0.675 g |
| 2-Methyl-5-N-(β-hydroxyethylamino)phenol | 0.501 g |
| Polyglycerolated oleyl alcohol containing 2 mol of glycerol | 4.0 g |
| Polyglycerolated oleyl alcohol containing 4 mol of glycerol (78% of AM) | 5.7 g AM |
| Oleic acid | 3.0 g |
| Oleyl amine containing 2 mol of ethylene oxide, sold under the name Ethomeen 012 by the company AKZO | 7.0 g |
| Diethylaminopropyl laurylaminosuccinamate sodium salt containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% of AM | 0.4 g AM |
| Ammonium acetate | 0.8 g |
| Antioxidant, sequestering agent | qs |
| Fragrance, preserving agent | qs |
| Aqueous ammonia containing 20% of NH$_3$ | 10.0 g |
| Demineralized water qs | 100 g |

At the time of use, this composition was mixed weight for weight with 20 volumes of hydrogen peroxide (6% by weight), which had a pH of 3. A mixture having a pH of 9.8 was obtained.

This mixture was then applied to grey hair containing 90% white hairs, for 30 minutes. After rinsing, washing with shampoo, rinsing and drying, the inventors believe that the hair would be dyed a red-purple shade which would particularly resist shampoos remarkably well.

EXAMPLE 2

The following dye composition, in accordance with the invention, was prepared:

| | |
|---|---|
| 2-(β-Hydroxyethyloxy)-para-phenylenediamine dihydrochloride | 0.723 g |
| 2-Methyl-5-N-(β-hydroxyethylamino)phenol | 0.501 g |
| Polyglycerolated oleyl alcohol containing 2 mol of glycerol | 4.0 g |
| Polyglycerolated oleyl alcohol containing 4 mol of glycerol (78% of AM) | 5.7 g AM |
| Oleic acid | 3.0 g |
| Oleyl amine containing 2 mol of ethylene oxide, sold under the name Ethomeen 012 by the company AKZO | 7.0 g |
| Diethylaminopropyl laurylaminosuccinamate sodium salt containing 55% of AM | 3.0 g AM |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite in aqueous solution containing 35% of AM | 0.4 g AM |
| Ammonium acetate | 0.8 g |
| Antioxidant, sequestering agent | qs |
| Fragrance, preserving agent | qs |
| Aqueous ammonia containing 20% of NH$_3$ | 10.0 g |
| Demineralized water qs | 100 g |

At the time of use, this composition was mixed weight for weight with 20 volumes of hydrogen peroxide (6% by weight), which had a pH of 3. A mixture having a pH of 9.8 was obtained.

This mixture was then applied to grey hair containing 90% white hairs, for 30 minutes. After rinsing, washing with shampoo, rinsing and drying, the inventors believe the hair would be dyed a purple shade which would particularly resist shampoos remarkably well.

What is claimed is:

1. A composition for the oxidation dyeing of keratinous fibres, comprising a medium suitable for dyeing, said medium containing at least one para-phenylenediamine oxidation dye precursor, said precursor being a compound of formula (I):

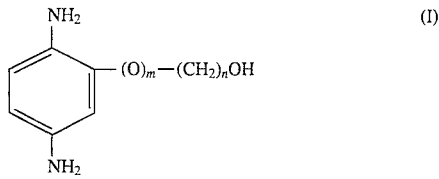

in which m is an integer equal to zero, and n is an integer ranging from 1 to 4 inclusively;
or an acid addition salt thereof; and at least one meta-aminophenol coupling agent, said coupling agent being a compound of formula (II):

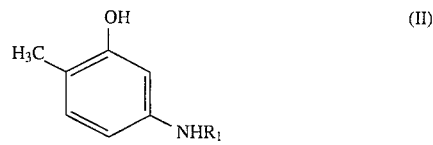

in which R$_1$ represents an alkyl radical containing from 1 to 2 carbon atoms
or a β-hydroxyalkyl radical containing from 2 to 3 carbon atoms;
or an acid addition salt thereof;

wherein said at least one para-phenylenediamine oxidation dye precursor and said at least one meta-aminophenol coupling agent are present in amounts effective to react with an oxidation agent to dye said fibres, with the proviso that when, in formula (II), R$_1$ represents β-hydroxyethyl radical, said dye composition is free of an additional oxidation dye precursor selected from 3-methyl-para-aminophenol, 2-methyl-para-aminophenol and 2-hydroxymethyl-para-aminophenol.

2. A dyeing composition according to claim 1, wherein said at least one para-phenylenediamine oxidation dye precursor is 2-(hydroxymethyl)-para-phenylenediamine, 2-(β-hydroxyethyl)-para-phenylenediamine, or an acid addition salt of any of said compounds.

3. A dyeing composition according to claim 1, wherein said at least one meta-aminophenol coupling agent is 2-methyl-5-N-(βhydroxyethylamino)-phenol or an acid addition salt thereof.

4. A dyeing composition according to claim 1 wherein said at least one para-phenylenediamine oxidation dye precursor is 2(β-hydroxyethyl)-para-phenylenediamine or an acid addition salt thereof, and wherein said at least one meta-aminophenol coupling agent is 2-methyl-5-N-(β-hydroxyethylamino)-phenol or an acid addition salt thereof.

5. A dyeing composition according to claim 1, wherein said acid addition salt of said dye precursor and said acid addition salt of said coupling agent are independently selected from hydrochlorides, sulphates, hydrobromides and tartrates.

6. A dyeing composition according to claim 1, wherein said para-phenylenediamine oxidation dye precursor of formula (I), or an acid addition salt thereof, is present in a concentration ranging from 0.01% to 10% by weight relative to the total weight of the composition, and said meta-aminophenol coupling agent of formula (II), or an acid addition salt thereof, is present in a concentration ranging from 0.005% to 3% by weight relative to the total weight of the composition.

7. A dyeing composition according to claim 6, wherein said para-phenylenediamine oxidation dye precursor of formula (I), or an acid addition salt thereof, is present in a concentration ranging from 0.05% to 5% by weight relative to the total weight of the composition, and said meta-aminophenol coupling agent of formula (II), or an acid addition salt thereof, is present in a concentration ranging from 0.05% to 2% by weight relative to the total weight of the composition.

8. A dyeing composition according to claim 1, wherein said keratinous fibres are human keratinous fibres.

9. A dyeing composition according to claim 1, which is a ready-to-use composition, which further comprises an oxidizing agent and has a pH ranging from 3 to 11.

10. A process for dyeing keratinous fibres, comprising the steps of:
(I) applying to said fibres the dyeing composition according to claim 1; and
(II) developing the colour or said dyeing composition in an acidic, neutral or alkaline medium, by applying said oxidizing agent to said fibres simultaneously with or subsequent to said dyeing composition.

11. A process according to claim 10, wherein said oxidizing agent is added to said dyeing composition at the time of applying in said step (i).

12. A process according to claim 10, wherein said dyeing composition is contained in a composition (A), and said oxidizing agent is separately contained in a composition (B), and wherein said separate compositions (A) and (B) are applied to said fibres simultaneously.

13. A process according to claim 10, wherein said dyeing composition is contained in a composition (A), and said oxidizing agent is separately contained in a composition (B), and wherein said composition (B) is separately applied to said fibers subsequent to said application of said dyeing composition (A).

14. A process according to claim 10, wherein said keratinous fibres are human keratinous fibres.

15. A kit for dyeing keratinous fibres comprising at least two compartments, one of said compartments containing a dyeing composition (A) according to claim 1, and another of said compartments containing a composition (B) containing an oxidizing agent in a medium suitable for dyeing.

16. A kit according to claim 15, wherein said keratinous fibres are human keratinous fibres.

17. A process for dyeing keratinous fibres comprising the steps of:
(i) applying to said fibres a dyeing composition (A) comprising a composition according to claim 1, said dyeing composition being obtained from a kit for dyeing keratinous fibres comprising at least two compartments, òne of said compartments containing a dyeing composition according to claim 1 and another of said compartments containing a composition (B) containing an oxidizing agent in a medium appropriate for dyeing; and
(ii) developing the colour of said dyeing composition in said medium by applying said composition (B) containing said oxidizing agent to said fibres simultaneously with or subsequent to said dyeing composition (A).

18. A process according to claim 17, wherein said composition (B) containing said oxidizing agent is applied to said fibres simultaneously with said dyeing composition (A).

19. A process according to claim 17, wherein said composition (B) containing said oxidizing agent is applied to said fibres subsequent to said dyeing composition (A).

20. A process according to claim 17, wherein said keratinous fibres are human keratinous fibres.

21. A composition for the oxidation dyeing of keratinous fibres, comprising a medium suitable for dyeing, said medium containing
at least one para-phenylenediamine oxidation dye precursor, said precursor being 2-(β-hydroxyethyl)-para-phenylenediamine or an acid addition salt thereof; and
at least one meta-aminophenol coupling agent, said coupling agent being 2-methyl-5-N-(β-hydroxyethylamino)-phenol or an acid addition salt thereof;
wherein said at least one para-phenylenediamine oxidation dye precursor and said at least one meta-aminophenol coupling agent are present in amounts effective to react with an oxidation agent to dye said fibres, and
with the proviso that said dye composition is free of an additional oxidation dye precursor selected from 3-methyl-para-aminophenol,2-methyl-para-aminophenol and 2-hydroxymethyl-para-aminophenol.

* * * * *

UNITED STATES PATENT AND TRADEMARK OFFICE
CERTIFICATE OF CORRECTION

PATENT NO. : 5,538,516
DATED : July 23, 1996
INVENTOR(S) : Marie-Pascale AUDOUSSET et al.

It is certified that error appears in the above-indentified patent and that said Letters Patent is hereby corrected as shown below:

On the Title Page, column 1, line 2, under "Inventors:", "Verneuil s/Seine" should read --Verneuil S/Seine--.

In the Claims, claim 3, column 7, line 10, "(Bhydroxyethylamino)" should read --($\beta$-hydroxyethylamino)--;

claim 10, column 7, and 50, "(I)" and "(II)" should read --(i)-- and --(ii)--, respectively; and claim 15, column 8, line 11, after "(A)", insert --comprising a composition--.

Signed and Sealed this

Nineteenth Day of November, 1996

Attest:

BRUCE LEHMAN

Attesting Officer

Commissioner of Patents and Trademarks